United States Patent
Farmer et al.

(10) Patent No.: US 11,414,640 B2
(45) Date of Patent: Aug. 16, 2022

(54) MATRIX FERMENTATION SYSTEMS AND METHODS FOR PRODUCING MICROBE-BASED PRODUCTS

(71) Applicant: Locus IP Company, LLC, Solon, OH (US)

(72) Inventors: Sean Farmer, North Miami Beach, FL (US); Ken Alibek, Solon, OH (US); Sharmistha Mazumder, Copley, OH (US); Maja Milovanovic, North Royalton, OH (US); Alibek Moldakozhayev, Solon, OH (US)

(73) Assignee: LOCUS IP COMPANY, LLC, Solon, OH (US)

( * ) Notice: Subject to any disclaimer, the term of this patent is extended or adjusted under 35 U.S.C. 154(b) by 239 days.

(21) Appl. No.: 16/760,219

(22) PCT Filed: Oct. 31, 2018

(86) PCT No.: PCT/US2018/058412
§ 371 (c)(1),
(2) Date: Apr. 29, 2020

(87) PCT Pub. No.: WO2019/089730
PCT Pub. Date: May 9, 2019

(65) Prior Publication Data
US 2021/0180000 A1 Jun. 17, 2021

Related U.S. Application Data

(60) Provisional application No. 62/579,271, filed on Oct. 31, 2017, provisional application No. 62/610,437, filed on Dec. 26, 2017, provisional application No. 62/611,275, filed on Dec. 28, 2017, provisional application No. 62/632,133, filed on Feb. 19, 2018, provisional application No. 62/632,193, filed on Feb. 19, 2018, provisional application No. 62/655,891, filed on Apr. 11, 2018.

(51) Int. Cl.
| | |
|---|---|
| *C12N 1/14* | (2006.01) |
| *C12M 1/00* | (2006.01) |
| *C12N 1/16* | (2006.01) |
| *C12N 9/24* | (2006.01) |
| *C12P 1/02* | (2006.01) |
| *C12P 7/64* | (2022.01) |
| *C12P 19/04* | (2006.01) |

(52) U.S. Cl.
CPC .......... *C12M 41/14* (2013.01); *C12M 1/005* (2013.01); *C12N 1/16* (2013.01); *C12N 9/2402* (2013.01); *C12P 1/02* (2013.01); *C12P 7/64* (2013.01); *C12P 19/04* (2013.01); *C12Y 302/01006* (2013.01); *C12Y 302/01014* (2013.01)

(58) Field of Classification Search
CPC ............... C12N 1/14; C12N 1/16; C12N 1/20
See application file for complete search history.

(56) References Cited

U.S. PATENT DOCUMENTS

| | | | |
|---|---|---|---|
| 4,332,904 | A | 6/1982 | Kurane et al. |
| 6,261,811 | B1 | 7/2001 | Hamdy |
| 6,524,631 | B1 | 2/2003 | Dicks |
| 8,361,778 | B2 | 1/2013 | Bergmaier |
| 2005/0266036 | A1 | 12/2005 | Awada et al. |
| 2008/0020437 | A1 | 1/2008 | Savarese |
| 2008/0229657 | A1 | 9/2008 | Senyk et al. |
| 2009/0280212 | A1 | 11/2009 | Sugimoto et al. |
| 2010/0064746 | A1 | 3/2010 | Medoff |
| 2011/0044972 | A1 | 2/2011 | Fieldhouse et al. |
| 2011/0200572 | A1 | 8/2011 | Reuter |
| 2012/0058895 | A1 | 3/2012 | Awada et al. |
| 2012/0220464 | A1 | 8/2012 | Giessler-Blank et al. |
| 2013/0260450 | A1 | 10/2013 | Fey et al. |
| 2013/0324406 | A1 | 12/2013 | Chisholm et al. |
| 2015/0037302 | A1 | 2/2015 | Bralkowski et al. |
| 2015/0044356 | A1 | 2/2015 | Bootsma et al. |
| 2015/0045290 | A1 | 2/2015 | Coutte et al. |
| 2015/0305347 | A1 | 10/2015 | Wicks et al. |
| 2016/0083705 | A1 | 3/2016 | Milos |
| 2016/0106117 | A1 | 4/2016 | Gazenko |

(Continued)

FOREIGN PATENT DOCUMENTS

| | | |
|---|---|---|
| CN | 102533597 A | 7/2012 |
| CN | 102613252 A | 8/2012 |
| CN | 102839121 A | 12/2012 |

(Continued)

OTHER PUBLICATIONS

Banat, I.M., et al., "Cost effective technologies and renewable substrates for biosurfactants' production." Frontiers in Microbiology, Dec. 2014, 5(697): 1-18.

(Continued)

*Primary Examiner* — Tekchand Saidha
(74) *Attorney, Agent, or Firm* — Saliwanchik, Lloyd & Eisenschenk

(57) ABSTRACT

The subject invention provides methods of producing advantageous microbes and/or by-products using a modified form of solid-state fermentation, or matrix fermentation. In particular, the methods utilize foodstuff mixed with liquid nutrient medium to produce a three-dimensional scaffold substrate having ample surface area on which the microbes can grow. The methods can be used to cultivate yeasts, fungi and bacteria at high concentrations without susceptibility to total contamination. The subject invention can be used in remote locations and can be transported with ease.

19 Claims, No Drawings

(56) References Cited

U.S. PATENT DOCUMENTS

2016/0145660 A1   5/2016   Campoy Garcia et al.

FOREIGN PATENT DOCUMENTS

| CN | 105087383 A | 11/2015 |
| CN | 106135503 A | 11/2016 |
| EP | 2390345 A1 | 11/2011 |
| EP | 3029147 A1 | 6/2016 |
| KR | 20170132149 A | 12/2017 |
| WO | 9525163 A1 | 9/1995 |
| WO | 03093408 A1 | 11/2003 |
| WO | 2004020647 A1 | 3/2004 |
| WO | 2010055093 A1 | 5/2010 |
| WO | 2015089183 A2 | 6/2015 |
| WO | 2017035101 A1 | 3/2017 |
| WO | 2017044953 A1 | 3/2017 |

OTHER PUBLICATIONS

Lee, C.K., et al., "Efficiency of Developed Solid State Bioreactor 'FERMSOSTAT' on Cellulolytic and Xylanase Enzymes Production." Sains Malaysiana, 2017, 46(8): 1249-1257.

Ohno, A., et al., "Production of the Antifungal Peptide Antibiotic, Iturin by Bacillus subtilis NB22 in Solid State Fermentation." Journal of Fermentation and Bioengineering, 1993, 75(1): 23-27.

Ohno, A., et al., "Production of a Lipopeptide Antibiotic, Surfactin, by Recombinant Bacillus subtilis in Solid State Fermentation." Biotechnology and Bioengineering, 1995, 47: 209-214.

De Brito, D., Biosurfactants from renewable raw materials, Universidade do Minho Departamento de Engenharia Biologica, Nov. 2013, pp. 1-93.

De Oliveira, M., et al., "Review: Sophorolipids a Promising Biosurfactant and it's Applications." International Journal of Advanced Biotechnology and Research, 2015, 6(2): 161-174.

Santos, D., et al., "Biosurfactants: Multifunctional Biomolecules of the 21st Century " International Journal of Molecular Sciences. 2016,17(401): 1-31.

Sen, R., "Biosurfactants: Advances in Experimental Medicine and Biology." Landes Bioscience and Springer Science +Business Media, LLC, 2010, 672: 1-331.

MATRIX FERMENTATION SYSTEMS AND METHODS FOR PRODUCING MICROBE-BASED PRODUCTS

CROSS-REFERENCE TO RELATED APPLICATIONS

This application is a National Stage Application of International Application No. PCT/US2018/058412, filed Oct. 31, 2018; which claims priority to U.S. Provisional Patent Applications No. 62/579,271, filed Oct. 31, 2017; No. 62/610,437, filed Dec. 26, 2017; No. 62/611,275, filed Dec. 28, 2017; No. 62/632,133, filed Feb. 19, 2018; No. 62/632,193, filed Feb. 19, 2018; and No. 62/655,891, filed Apr. 11, 2018, each of which is incorporated by reference herein in its entirety.

BACKGROUND OF THE INVENTION

Microorganisms, such as bacteria, are important for the production of a wide variety of useful bio-preparations. These microbes and their by-products are useful in many settings, such as oil production; agriculture; remediation of soils, water and other natural resources; mining; animal feed; waste treatment and disposal; food and beverage preparation and processing; and human health.

Interest in microbial surfactants, i.e., biosurfactants, in particular, has been steadily increasing in recent years due to their diversity, environmentally-friendly nature, selectivity, performance under extreme conditions, and potential applications in environmental protection. Biosurfactants reduce the interfacial tension between water and oil and, therefore, lower the hydrostatic pressure required to move entrapped liquid to overcome the capillary effect. Biosurfactants also contribute to the formation of micelles, providing a physical mechanism to mobilize, for example, oil in a moving aqueous phase. Biosurfactants also enhance the emulsification of hydrocarbons, have the potential to solubilize hydrocarbon contaminants, and increase their availability for microbial degradation.

The use of chemicals for the treatment of a hydrocarbon-polluted site may contaminate the environment, whereas biological treatments may efficiently remove pollutants, while being biodegradable themselves. Hence, biosurfactant-producing microorganisms may play an important role in the accelerated bioremediation of hydrocarbon-contaminated sites. These compounds can also be used in enhanced oil recovery as well as for other applications, including herbicides and pesticides, detergents, healthcare and cosmetics, pulp and paper, coal, textiles, ceramic processing, food industries, uranium ore-processing, and mechanical dewatering of peat.

Thus, there exists an enormous potential for the use of microbes in a broad range of industries. One limiting factor in commercialization of microbe-based products has been the cost per propagule density, where it is particularly expensive and unfeasible to apply microbial products to large scale operations with sufficient inoculum to see the benefits. This is partly due to the difficulties in cultivating efficacious microbial products on a large scale.

Two principle forms of microbe cultivation exist for growing bacteria, yeasts and fungi: submerged (liquid fermentation) and surface cultivation (solid-state fermentation (SSF)). Both cultivation methods require a nutrient medium for the growth of the microorganisms, but they are classified based on the type of substrate used during fermentation (either a liquid or a solid substrate). The nutrient medium for both types of fermentation typically includes a carbon source, a nitrogen source, salts and other appropriate additional nutrients and microelements.

In particular, SSF utilizes solid substrates, such as bran, bagasse, and paper pulp, for culturing microorganisms. One advantage to this method is that nutrient-rich waste materials can be easily recycled as substrates. Additionally, the substrates are utilized very slowly and steadily, so the same substrate can be used for long fermentation periods. Hence, this technique supports controlled release of nutrients. SSF is best suited for fermentation techniques involving fungi and microorganisms that require less moisture content; however, it cannot be used in fermentation processes involving organisms that require high water activity, such as certain bacteria.

Submerged fermentation, on the other hand, is typically better suited for those microbes that require high moisture. This method utilizes free flowing liquid substrates, such as molasses and nutrient broth, into which bioactive compounds are secreted by the growing microbes. While submerged cultivation can be achieved relatively quickly, it does possess certain drawbacks. For example, the substrates are utilized quite rapidly, thus requiring constant replenishment and/or supplementation with nutrients. Additionally, it requires more energy, more stabilization, more sterilization, more control of contaminants, and often a more complex nutrient medium than is required for SSF. Furthermore, transporting microorganisms produced by submerged cultivation can be complicated and costly, in addition to the difficulty for laborers to implement the process in the field, e.g., in a remote location where the product will be used.

Microbes have the potential to play highly beneficial roles in, for example, the oil and agriculture industries; however, methods are needed for making microbe-based products more readily available, and preferably in a form that can be produced in, or transported to, remote areas without loss of efficacy.

BRIEF SUMMARY OF THE INVENTION

This invention relates to the production of solid state microbe-based products for commercial application. Specifically, the subject invention provides methods and systems for the efficient production of beneficial microbes, as well as for the production and use of substances, such as metabolites, derived from these microbes and the substrate in, or on, which they are produced. Methods are also provided for using these microbe-based products. Advantageously, the subject invention can be used as a "green" process for producing microorganisms and their metabolites on a large scale and at low cost, without releasing harmful chemicals into the environment.

In preferred embodiments, the subject invention provides systems, methods and materials for cultivating a wide variety of microbes and also for producing microbe-based products. In one embodiment, the methods can be used to cultivate inocula for producing microbe-based products on an industrial scale.

In preferred embodiments, the subject invention provides methods of cultivating a microorganism and/or a microbial growth by-product using a novel form of solid state fermentation, or matrix fermentation. Advantageously, the cultivation methods can be scaled up or down in size. Most notably, the methods can be scaled to an industrial scale, meaning a scale that is capable of supplying microbe-based products in amounts suitable for commercial applications, e.g., oil and/or gas recovery, bioleaching, agriculture, livestock production, and aquaculture.

The subject invention does not require fermentation systems having sophisticated aeration systems, mixers, or probes for measuring and/or stabilizing DO, pH and other fermentation parameters.

In preferred embodiments, the method of cultivating a microorganism and/or producing a microbial growth by-product comprises: a) placing a solid substrate, optionally mixed with nutrients to enhance microbial growth, into a container to form a matrix; b) applying an inoculant of a microorganism to the matrix; c) placing the container with the inoculated matrix into an incubation space; and d) incubating the container at a temperature between 25-40° C. for an amount of time to allow the microorganism to grow through the matrix.

In certain embodiments, the solid substrate comprises a plurality of individual solid items, e.g., pieces, morsels, grains or particles. In preferred embodiments, the solid items are foodstuff. The foodstuff can include one or more of, for example, rice, beans, lentils, legumes, oats and oatmeal, corn and other grains, pasta, wheat bran, flours or meals (e.g., corn flour, nixtamilized corn flour, partially hydrolyzed corn meal), and/or other similar foodstuff to provide surface area for the microbial culture to grow and/or feed on.

In one embodiment, wherein the matrix comprises pre-made pasta, the pasta can be made from, for example, corn flour, wheat flour, semolina flour, rice flour, quinoa flour, potato flour, soy flour, chickpea flour and/or combinations thereof. Advantageously, the microbes can grow inside the pasta and/or on outside surfaces of the pasta.

In one embodiment, the method of cultivation comprises preparing the container, which can be, e.g., a tray, a metal sheet pan or a steam pan fitted for a standard proofing oven. Preparation can comprise covering the inside of the containers with, for example, foil. Preparation can also comprise sterilizing the containers by, for example, autoclaving them. Lids, as well as silicon bands, can be provided for sealing the containers, if desired.

Next, a matrix is formed by mixing a foodstuff and a liquid medium comprising additional salts and/or nutrients to support microbial growth. The mixture is then spread into the containers and layered to form a matrix with a thickness of approximately 1 to 12 inches, preferably, 1 to 6 inches.

In preferred embodiments, the matrix substrate serves as a three-dimensional scaffold that provides ample surface area on which microbes can grow. In some embodiments, the foodstuff in the matrix can also serve as a source of nutrients for the microbes. Furthermore, the matrix can provide increased access to oxygen supply when a microorganism requires cultivation under aerobic conditions.

In one embodiment, grooves, ridges, channels and/or holes can be formed in the matrix to increase the surface area upon which the microorganisms can grow. This also increases the depth of microbial growth within the substrate and provides enhanced oxygen penetration throughout the culture during aerobic cultivation.

In one embodiment, when a motile microorganism is being cultivated, the method can further comprise applying a motility enhancer, such as potato extract and/or banana peel extract, to the matrix to increase the speed of microbial motility and distribution throughout the matrix.

Sterilization of the containers and matrix can be performed after the matrix has been placed into the container. Sterilization can be performed by autoclave or any other means known in the art. In some embodiments, when, for example, pasta is used as the solid substrate, this process can also effectively cook the substrate. To create a completely sterile system, lids and bands can also be sterilized.

In one embodiment, when a flour or a meal is used as the solid substrate, the method can comprise sectioning or chopping the matrix into chunk. Flours and meals can create a denser matrix than foodstuff having larger individual pieces, especially after it has been subjected to sterilization. Thus, breaking up the dense substrate prior to seeding with a microorganism increases the surface area for microbial growth.

After preparation, the matrix in the container can be inoculated with a desired microorganism that is optionally pre-mixed with sterile nutrient medium. Optionally, depending upon the aeration needs of the microorganism being cultivated, the containers can then be sealed with, for example, the lids and bands. When, for example, an anaerobic microbe is being produced, aeration is not needed and the container can be sealed.

The inoculum preferably comprises vegetative cells, spores, conidia, or other propagules of a desired microorganism, which can be cultivated beforehand using any known fermentation method. In one embodiment, inoculation is performed by applying the inoculum uniformly onto the surface of the matrix. The inoculum can applied via, for example, spraying, sprinkling, pouring, injecting, pipetting or spreading.

The containers with inoculated matrix can then be placed inside an incubation space. In one embodiment, the incubation space is a fermentation reactor. In one embodiment, the fermentation reactor is a proofing oven, such as, for example, a standard proofing oven used in commercial baking. In one embodiment, the incubation space is a thermostable room or enclosure comprising walls, a floor and a ceiling.

Optionally, the incubation space can be equipped with a conveyer system, wherein the inoculated containers move continuously through the space at a speed allowing for culture to grow using, for example, a conveyer belt or a pulley system.

Fermentation parameters within the incubation space can be adjusted based on the desired product to be produced (e.g., the desired microbial growth by-product) and the microorganism being cultivated. Advantageously, in one embodiment, it is not necessary to monitor or stabilize the pH of the culture.

In one embodiment, the incubation space can optionally comprise an aeration system to provide slow motion air supply. The use of an aeration system depends upon the needs of the microorganism being cultivated.

In one embodiment, the use of passive exchange of ambient air can be sufficient to supply the necessary oxygenation to an aerobic culture and to standardize the concentration of air within the incubation space. In one embodiment, this passive air exchange system comprises an inlet, optionally with an air filter, through which ambient air travels into the incubation space, and an outlet, through which air exits the space.

In some embodiments, a vacuum and/or pump system provides air exchange into and out of the incubation space.

In some embodiments, individual containers can comprise inlets and outlets for air exchange. For example, in one embodiment, a container sealed with a lid can comprise an inlet and an outlet fixed to the lid, wherein an air pump supplies slow motion air into the sealed container through tubing attached to the inlet, and air exits the container through tubing attached to the outlet.

The temperature within the incubation space is preferably kept between about 25-40° C. In one embodiment, the temperature is kept at about 25-35° C. In one embodiment, the temperature is kept at about 32-37° C. The exact temperature range will vary depending upon the microorganism being cultivated.

The culture can be incubated for an amount of time that allows for the microorganism to grow and reach a desired concentration. In one embodiment, when the culture is a spore-forming microbe, the incubation time is preferably long enough for the culture to reach 50% to 100% sporulation.

In preferred embodiments, the amount of incubation time is from 1 day to 14 days, more preferably, from 2 days to 10 days.

The containers may be sprayed regularly throughout fermentation (e.g., once a day, once every other day, once per week) with a sterile nutrient medium to increase microbial concentration. In some embodiments, the microorganisms will consume either a portion of, or the entirety of, the matrix substrate throughout fermentation.

The culture and remaining substrate can be harvested from the containers, then blended together to produce a microbial slurry. The microbial slurry can comprise the microbes, their growth by-products, and any remaining nutrients and substrate. The microbial slurry can be processed and further ingredients, e.g., additional nutrients, can be added as deemed necessary for the intended use of the microbe-based product. The concentration of microbes produced according to the subject methods can reach at least $1\times10^8$ cells per gram, preferably, from $1\times10^{10}$ to $1\times10^{12}$ cells, spores or other propagules per gram.

In one embodiment, the microbial slurry is homogenized and dried to produce a dry microbe-based product. Drying can be performed using standard methods in the art, including, for example, spray drying or lyophilization.

In one embodiment, the microbial slurry can be utilized directly, without drying or processing. In another embodiment, the microbial slurry can be mixed with water to form a liquid microbe-based product.

In some embodiments, the various formulations of microbe-based product produced according to the subject methods can be stored prior to their use.

In one embodiment, the systems and methods of the subject invention can be used to produce a microbial metabolite, wherein the microbial slurry is mixed with water or another solvent, and this slurry-solvent mixture is filtered to separate solid portions of the mixture from liquid portions. The extracted liquid, which comprises the microbial metabolite, can then be purified further, if desired, using, for example, centrifugation, rotary evaporation, microfiltration, ultrafiltration and/or chromatography.

The metabolite and/or growth by-product can be, for example, a biosurfactant, enzyme, biopolymer, acid, solvent, amino acid, nucleic acid, peptide, protein, lipid and/or carbohydrate. In certain embodiments, the growth by-product is a biosurfactant, such as a glycolipid or a lipopeptide.

In certain embodiments, the subject invention provides microbe-based products, as well as their uses in a variety of settings including, for example, oil and gas production; bioremediation and mining; waste disposal and treatment; animal health (e.g., livestock production and aquaculture); plant health and productivity (e.g., agriculture, horticulture, crops, pest control, forestry, turf management, and pastures); and human health (e.g., supplements, nutraceuticals and cosmetics).

Organisms that can be cultured using the materials and methods of the subject invention can include, for example, yeasts, fungi, bacteria, and archaea.

In some embodiments, the microorganisms are yeasts, such as, for example, *Starmerella bombicola, Wickerhamomyces anomalus, Pseudozyma* spp., *Saccharomyces* spp. or *Pichia* spp. yeasts. In some embodiments, the microorganisms are fungi, such as, for example, *Trichoderma* spp., as well as mushrooms such as *Lentinula edodes* (shiitake).

In some embodiments, the microorganisms are bacteria. The bacteria can be anaerobic, aerobic, microaerophilic, facultative anaerobes and/or obligate aerobes. In one embodiment, the bacteria are spore-forming bacteria. Non-limiting examples of bacteria include *Bacillus* spp. (e.g., *Bacillus subtilis, Bacillus licheniformis, Bacillus amyloliquefaciens* and *Bacillus coagulans* GBI-30 (BC30)), *Pseudomonas* spp., and *Azotobacter* spp.

The microbe-based products produced according to the methods of the subject invention can comprise the microorganisms themselves and/or their growth by-products, and nutrients for microbial growth. The microorganisms can be live, viable or in an inactive form. They can be in the form of vegetative cells, spores, conidia, hyphae, mycelia and/or a combination thereof.

Advantageously, the subject systems and methods are not susceptible to total contamination by, for example, bacteriophages, as is the case for submerged fermentation methods. This is because the growth of microbes occurs at a slower rate than that of submerged culture. Furthermore, because the methods do not involve mixing of the culture as is done in submerged culture, a contaminant will remain isolated at a single location instead of spreading throughout the entire culture.

Additional advantages to using the subject methods include reduced water and energy consumption; transportability and ease of use, even in remote areas; and simple collection of useful microbial products due to the fact that the microorganism is not dispersing into a liquid medium, but instead growing on a stationary, solid matrix.

DETAILED DESCRIPTION

The subject invention provides methods and systems for the efficient production of beneficial microbes, as well as for the production and use of substances, such as metabolites, derived from these microbes and the substrate in, or on, which they are produced. Methods are also provided for using these microbe-based products. Advantageously, the subject invention can be used as a "green" process for producing microorganisms and their metabolites on a large scale and at low cost, without releasing harmful chemicals into the environment.

In preferred embodiments, the subject invention provides systems, methods and materials for cultivating a variety of microbe-based products. In one embodiment, the methods can be used to cultivate inocula for producing microbe-based products on an industrial scale.

In certain embodiments, the subject invention provides microbe-based products, as well as their uses in a variety of settings including, for example, oil and gas production; bioremediation and mining; waste disposal and treatment; animal health (e.g., livestock production and aquaculture); plant health and productivity (e.g., agriculture, horticulture, crops, pest control, forestry, turf management, and pastures); and human health (e.g., nutraceuticals, supplements and cosmetics).

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with medium in which they were grown, in the microbe-based composition. The cells may be present at, for example, a concentration of at least $1 \times 10^4$, $1 \times 10^5$, $1 \times 10^6$, $1 \times 1 \times 10^7$, $1 \times 10^8$, $1 \times 10^9$, $1 \times 10^{10}$, $1 \times 10^{11}$, $1 \times 10^{12}$ or $1 \times 10^{13}$ or more cells per gram or milliliter of the composition.

The subject invention further provides "microbe-based products," which are products that are to be applied in practice to achieve a desired result. The microbe-based product can be simply the microbe-based composition harvested from the microbe cultivation process. Alternatively, the microbe-based product may comprise only a portion of the product of cultivation (e.g., only the growth by-products), and/or the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as amino acids, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. An isolated microbial strain means that the strain is removed from the environment in which it exists in nature. Thus, the isolated strain may exist as, for example, a biologically pure culture, or as spores (or other forms of propagule) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, enzymes, toxins, acids, solvents, alcohols, proteins, vitamins, minerals, microelements, amino acids, polymers, and surfactants.

As used herein, the term "plurality" refers to any number or amount greater than one.

As used herein, the term "probiotic" refers to microorganisms, which, when administered in adequate amounts, confer a health benefit on the host. The probiotics may be available in foods and dietary supplements (for example through capsules, tablets, and powders). Non-limiting examples of foods containing probiotics include dairy products such as yogurt, fermented and unfermented milk, smoothies, butter, cream, hummus, kombucha, salad dressing, miso, tempeh, nutrition bars, and some juices and soy beverages. In preferred embodiments, the microorganisms are live or in the spore form.

As used herein "reduction" means a negative alteration, and "increase" means a positive alteration, wherein the negative or positive alteration is at least 1%, 5%, 10%, 25%, 50%, 75%, or 100%.

By "reference" is meant a standard or control condition.

By "salt-tolerant" in reference to a particular microbial strain, means the strain is capable of growing in a sodium chloride concentration of 15% or greater. In a specific embodiment, "salt-tolerant" refers to the ability to grow in 150 g/L or more of NaCl.

By "surfactant" is meant compounds that lower the surface tension (or interfacial tension) between two liquids or between a liquid and a solid. Surfactants act as, e.g., detergents, wetting agents, emulsifiers, foaming agents, and dispersants. A "biosurfactant" is a surface-active substance produced by a living cell.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, or 20 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Growth of Microbes According to the Subject Invention

The subject invention provides methods for cultivation of microorganisms and production of microbial metabolites and/or other by-products of microbial growth using a novel form of solid state, or surface, fermentation. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules, polymers and excreted proteins), residual nutrients and/or intracellular components (e.g. enzymes and other proteins).

The methods of the subject invention utilize enclosed spaces for incubation of microbial cultures. In one embodiment, the incubation space is a fermentation reactor. In one embodiment, the fermentation reactor is a proofing oven, such as a standard oven used in commercial baking for, e.g., proofing dough.

In one embodiment, the incubation space is in the form of thermostable enclosure, such as a trailer or a room, that is equipped with the necessary components to provide, for example, a stable temperature and/or circulating air for the culture. The incubation space can optionally be equipped with an automated conveyor system for continuous production.

In one embodiment, the incubation space may optionally have functional controls/sensors or may be connected to functional controls/sensors to measure important factors in the cultivation process, such as pH, oxygen, pressure, temperature, agitator shaft power, humidity, viscosity and/or microbial density and/or metabolite concentration. Preferably, however, no such controls are necessary.

In a further embodiment, the incubation space may also be able to monitor the growth of microorganisms inside (e.g., measurement of cell number and growth phases). Alternatively, a daily sample may be taken from and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through, e.g., air pumps.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, canola oil, rice bran oil, olive oil, corn oil, sesame oil, and/or linseed oil; etc. These carbon sources may be used independently or in a combination of two or more.

In one embodiment, growth factors, trace nutrients and/or bio stimulants for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate (e.g., ferrous sulfate heptahydrate), iron chloride, manganese sulfate, manganese sulfate monohydrate, manganese chloride, zinc sulfate, lead chloride, copper sulfate, calcium chloride, calcium carbonate, and/or sodium carbonate. These inorganic salts may be used independently or in a combination of two or more.

In some embodiments, when, for example, the microbes used to inoculate the substrate are in spore form (e.g., bacterial endospores), germination enhancers can be added to the substrate. Examples of germination enhancers according to the subject invention include, but are not limited to, L-alanine, manganese, L-valine, and L-asparagine or any other known germination enhancer.

In some embodiments, when the microbe is a motile bacteria, motility enhancers can be added to the substrate, such as potato extract or banana peel extract.

In some embodiments, the method for cultivation may optionally comprise adding additional acids and/or antimicrobials in to the substrate before and/or during the cultivation process. Advantageously, however, the subject method reduces or eliminates the need for protection from contamination during cultivation due in part to the slower rate of microbial growth and the lack of continuous mixing of the culture.

The pH of the mixture should be suitable for the microorganism of interest, though advantageously, stabilization of pH using buffers or pH regulators is not necessary when using the subject cultivation methods.

The method and equipment for cultivation of microorganisms and production of the microbial by-products can be performed in a batch process or a quasi-continuous process.

In one embodiment, the method for cultivation of microorganisms is carried out at about 15 to 60° C., preferably, 25 to 40° C., and in specific embodiments, 25 to 35° C., or 32 to 37° C. In one embodiment, the cultivation may be carried out continuously at a constant temperature. In another embodiment, the cultivation may be subject to changing temperatures. Temperature ranges can vary depending on the microorganism being cultivated.

In one embodiment, the equipment and substrate can optionally be sterilized, for example, using an autoclave.

The cultivation equipment, such as the incubation space may be separated from, but connected to, a sterilizing unit, e.g., an autoclave. The cultivation equipment may also have a sterilizing unit that sterilizes in situ before starting the inoculation. Air can be sterilized by methods know in the art. For example, ambient air can pass through at least one filter before being introduced into the incubation space. In other embodiments, the nutrient medium may be pasteurized or, optionally, no heat at all added, where the use of low water activity and low pH may be exploited to control growth of contaminants.

In one embodiment, the subject invention further provides methods of producing a microbial metabolite by cultivating a microbe strain under conditions appropriate for growth and metabolite production. Optionally, the method can comprise purifying the metabolite. The subject invention provides methods of producing metabolites such as, e.g., biosurfactants, biopolymers, toxins, acids, alcohols, ethanol, lactic acid, beta-glucan, proteins, peptides, vitamins, minerals, microelements, amino acids, metabolic intermediates, polyunsaturated fatty acid, lipids and enzymes.

The microbial growth by-product produced by microorganisms of interest may be retained in the microorganisms or secreted into the substrate. The metabolite content can be, for example, at least 20%, 30%, 40%, 50%, 60%, 70%, 80%, or 90%.

In another embodiment, the method for producing microbial growth by-product may further comprise steps of concentrating and purifying the microbial growth by-product of interest. In a further embodiment, the substrate may contain compounds that stabilize the activity of microbial growth by-product.

In one embodiment, all of the microbial cultivation composition is removed upon the completion of the cultivation (e.g., upon, for example, achieving a desired spore density, or density of a specified metabolite). In this batch procedure, an entirely new batch is initiated upon harvesting of the first batch.

In another embodiment, only a portion of the fermentation product is removed at any one time. In this embodiment, biomass with viable cells remains as an inoculant for a new cultivation batch. The composition that is removed can be a cell-free substrate or contain cells. In this manner, a quasi-continuous system is created.

Matrix Fermentation

In preferred embodiments, the subject invention provides methods of cultivating a microorganism and/or a microbial growth by-product using a novel form of solid state fermentation, or matrix fermentation.

Advantageously, the subject invention does not require fermentation systems having sophisticated aeration systems, mixers, or probes for measuring and/or stabilizing DO, pH and other fermentation parameters.

In preferred embodiments, the method of cultivating a microorganism and/or producing a microbial growth by-product comprises: a) placing a solid substrate, optionally mixed with nutrients to enhance microbial growth, into a container to form a matrix; b) applying an inoculant of a microorganism to the matrix; c) placing the container with the inoculated matrix into an incubation space; and d) incubating the container at a temperature between 25-40° C. for an amount of time to allow the microorganism to grow through the matrix.

In preferred embodiments, the matrix according to the subject methods serves as a three-dimensional scaffold structure comprising a plurality of internal and external surfaces on which microbes can grow.

In certain embodiments, the matrix comprises a solid substrate, which is comprised of a plurality of individual solid items, e.g., pieces, morsels, grains, or particles. The individual solid items are arranged so as to create the scaffold structure of the matrix. Preferably, the solid items are capable of substantially retaining their shape and/or structure, even in the presence of a liquid. In some embodiments, the matrix is capable of substantially retaining its shape and/or structure as a whole, even though the solid substrate therein may be mixed with a liquid.

In some embodiments, substantially retaining shape and/or structure means retaining shape and/or structure to such a degree that the internal and external surfaces of the matrix, or total surface area thereof, are not compromised and remain exposed for microbes to colonize, and, in preferred embodiments, exposed to air and/or other gases.

In one embodiment, the plurality of solid items are preferably solid pieces, morsels, grains, or particles of foodstuff. The foodstuff can include one or more of, for example, rice, legumes, corn and other grains, oats and oatmeal, pasta, wheat bran, flours or meals (e.g., corn flour, nixtamilized corn flour, partially hydrolyzed corn meal), and/or other similar foodstuff to provide surface area for the microbial culture to grow and/or feed on.

In one embodiment, the foodstuff is a legume. Legumes include beans, nuts, peas and lentils. Examples of legumes according to the subject invention include but are not limited to chickpeas, runner beans, fava beans, adzuki beans, soybeans, Anasazi beans, kidney beans, butter beans, haricots, cannellini beans, flageolet beans, pinto beans, borlotti beans, black beans, peanuts, soy nuts, carob nuts, green peas, snow peas, snap peas, split peas, garden peas, and black, red, yellow, orange, brown and green lentils.

In one embodiment, wherein the matrix substrate comprises pre-made pasta, the pasta can be made from, for example, corn flour, wheat flour, semolina flour, rice flour, quinoa flour, potato flour, soy flour, chickpea flour and/or combinations thereof. In some embodiments, the pasta is made from an enriched flour. Advantageously, the microbes can grow inside the pasta and/or on outside surfaces of the pasta.

In some embodiments, the pasta can be in the shape of a long string or ribbon, e.g., spaghetti or fettuccini. In some embodiments, the pasta can be in the shape of, for example, a sheet, a shell, a spiral, a corkscrew, a wheel, a hollow tube, a bow, or any variation thereof. Advantageously, the microbes can grow inside the pasta and/or on outside surfaces of the pasta. This increases the surface area upon which the microorganisms can grow, increases the depth of microbial growth within the substrate, and provides enhanced oxygen penetration within the culture when needed.

Other examples of applicable pasta shapes include, but are not limited to, acini di pepe, anelli, angel hair, bucatini, campanelle, cappalletti, cavatappi, casarecce, cavatelli, conchiglie, ditalini, egg noodles, farfalle, farfalline, fettuccine, fideo, fusilli, gemelli, gigli, lasagna, lasagne, linguine, macaroni, mafalda, manicotti, orecchiette, orzo, pappardelle, pastina, penne, pipe rigate, pipette rigate, radiatori, rigatoni, rocchetti, rotelle, rotini, ruote, spaghetti, tagliatelle, tortiglioni, tripolini, tubini, vermicelli, ziti and any variation thereof.

In one embodiment, wherein the matrix comprises grains of rice, the matrix substrate can be prepared by mixing rice grains and a liquid medium comprising additional salts and/or nutrients to support microbial growth.

In some embodiments, the rice can be, for example, long grain, medium grain, short grain, white (polished), brown, black, basmati, jasmine, wild, arborio, matta, rosematta, red cargo, sticky, sushi, Valencia rice, and any variation or combination thereof.

In certain embodiments, the type of foodstuff utilized as the solid substrate will depend upon which microbe is being cultivated. For example, in one embodiment, *Trichoderma* spp. can be cultivated efficiently using corn flour or modified forms thereof, and in another embodiment, *Bacillus* spp. can be cultivated efficiently using rice. These microbial taxa are not limited to these specific substrates, however.

In one embodiment, the method of cultivation comprises preparing the containers, which can be, e.g., a tray, a metal sheet pan, a steam pan, a bucket, a basket, a pan, a plate, a flask, a cup, a tank, a barrel, a dish or a column, made of, for example, plastic, metal or glass.

In one embodiment, the container is a standard size metal sheet pan. Standard size sheet pans are typically 1" or less deep, and can be full-size (18"×26"), two-thirds size (15"× 21"), half-size (13"×18"), or quarter size (9"×13").

Other sizes that differ from the standard sizes can also be utilized. In one embodiment, the sheet pan is from 0.5" to 3" deep. In one embodiment, the sheet pan is 8 to 30" wide. In one embodiment, the sheet pan is 10" to 50" long.

In one embodiment, the container is a standard size metal steam pan. Standard size steam pans can have dimensions including, but not limited to, 4 to 12" wide, 6 to 20" long, and 2 to 8" deep.

Preparation can comprise covering the inside of the containers with, for example, foil. Preparation can also comprise sterilizing the containers by, for example, autoclaving them. Lids, as well as silicon bands, can be provided for sealing the containers, if desired.

Next, a matrix substrate is formed by mixing a foodstuff item and a liquid medium comprising additional salts and/or nutrients to support microbial growth. In a specific embodiment, the nutrient medium can comprise, for example, maltose or another carbon source, yeast extract or another source of protein, and sources of minerals, potassium, sodium, phosphorous and/or magnesium.

The mixture is then placed into the containers and layered to form a matrix with a thickness of approximately 0.5 to 12 inches, preferably, 1 to 6 inches, more preferably, 1 to 4 inches. The thickness of the matrix (e.g., the volume of substrate) can vary depending on the depth of the container in which is it being prepared.

In some embodiments, the foodstuff in the matrix can also serve as a source of nutrients for the microbes. Furthermore, the matrix can provide increased access to oxygen supply when a microorganism requires cultivation under aerobic conditions.

In one embodiment, grooves, ridges, channels and/or holes can be formed in the matrix to increase the surface area upon which the microorganisms can grow. This also increases the depth of microbial growth within the matrix and provides enhanced oxygen penetration throughout the culture during aerobic cultivation.

In one embodiment, when a motile microorganism is being cultivated, the method can further comprise applying a motility enhancer, such as potato extract and/or banana peel extract, to the matrix to increase the speed of microbial motility and distribution throughout the matrix.

Sterilization of the containers and matrix can then be performed after the matrix has been placed into the container. Sterilization can be performed by autoclave or any other means known in the art. In some embodiments, when, for example, pasta is used as the solid substrate, this process can also effectively cook the substrate. To create a completely sterile system, lids and bands can also be sterilized.

In one embodiment, when a flour or a meal is used as the solid substrate, the method can comprise sectioning or chopping the matrix into chunks. Flours and meals can create a denser matrix than foodstuff having larger individual pieces, especially after it has been subjected to sterilization. Thus, breaking up the dense substrate prior to seeding with a microorganism increases the surface area for microbial growth.

After preparation, the containers can be inoculated with a desired microorganism that is optionally pre-mixed with sterile nutrient medium. Optionally, depending upon the aeration needs of the microorganism being cultivated, the containers can then be sealed with, for example, the lids and bands. When, for example, an anaerobic microbe is being produced, aeration is not needed and the container can be sealed.

The inoculum preferably comprises vegetative cells, spores, conidia, or other propagules of a desired microorganism, which can be cultivated beforehand using any known fermentation method. In one embodiment, inoculation is performed by applying the inoculum uniformly onto the surface of the matrix. The inoculum can applied via, for example, spraying, sprinkling, pouring, injecting, pipetting or spreading.

The containers with the inoculated matrix can then be placed inside an incubation space. In one embodiment, the incubation space is a fermentation reactor. In one embodiment, the fermentation reactor is a proofing oven, such as, for example, a standard proofing oven used in commercial baking. In one embodiment, the fermentation reactor is a smaller sized oven, for example, the size of a toaster oven or a household kitchen oven.

In one embodiment, a plurality of reactors can be used, for example, a plurality of proofing ovens. In one embodiment, the reactors are distributable and portable. In a further embodiment, wherein a plurality of reactors is used, the plurality of reactors can be assembled onto a single platform for ease of transport.

In one embodiment, the incubation space is a thermostable room or enclosure comprising walls, a floor and a ceiling.

Optionally, the incubation space can be equipped with a conveyer system, wherein the inoculated containers move continuously through the space at a speed allowing for culture to grow using, for example, a conveyer belt or a pulley system.

Fermentation parameters within the incubation space can be adjusted based on the desired product to be produced (e.g., the desired microbial growth by-product) and the microorganism being cultivated. Advantageously, in one embodiment, it is not necessary to monitor or stabilize the pH of the culture.

In one embodiment, the incubation space can optionally comprise an aeration system to provide slow motion air supply. The use of an aeration system depends upon the needs of the microorganism being cultivated.

In one embodiment, the use of passive exchange of ambient air can be sufficient to supply the necessary oxygenation to an aerobic culture and to standardize the concentration of air within the incubation space. In one embodiment, this passive air exchange system comprises an inlet, optionally with an air filter, through which ambient air travels into the incubation space, and an outlet, through which air exits the space.

In some embodiments, a vacuum and/or pump system provides air exchange into and out of the incubation space.

In some embodiments, individual containers can comprise inlets and outlets for air exchange. For example, in one embodiment, a container sealed with a lid can comprise an inlet and an outlet fixed to the lid, wherein an air pump supplies slow motion air into the sealed container through tubing attached to the inlet, and air exits the container through tubing attached to the outlet.

The temperature within the incubation space is preferably kept between about 25-40° C. In one embodiment, the temperature is kept at about 25-35° C. In one embodiment, the temperature is kept at about 32-37° C. The exact temperature range will vary depending upon the microorganism being cultivated. The temperature can be controlled using, for example, standard heating and/or cooling systems.

The culture can be incubated for an amount of time that allows for the microorganism to grow and reach a desired concentration. In one embodiment, when the culture is a spore-forming microbe, the incubation time is preferably long enough for the culture to reach 50% to 100% sporulation.

In preferred embodiments, the amount of incubation time is from 1 day to 14 days, more preferably, from 2 days to 10 days.

The containers may be sprayed regularly throughout fermentation (e.g., once a day, once every other day, once per week) with a sterile nutrient medium to increase microbial concentration. In some embodiments, the microorganisms will consume either a portion of, or the entirety of, the matrix substrate throughout fermentation.

In one embodiment, the culture can be harvested from the matrix, wherein the microorganism and/or its growth by-products are washed out of the matrix and optionally subjected to further purification.

In preferred embodiments, the matrix and culture are harvested from the containers and blended together to produce a microbial slurry. The microbial slurry can comprise the microbes, their growth by-products, and any remaining substrate and nutrients. The microbial slurry can be processed and further ingredients, e.g., additional nutrients, can be added as deemed necessary for the intended use of the microbe-based product. The concentration of microbes produced according to the subject methods can reach at least $1 \times 10^8$ cells per gram, preferably, from $1 \times 10^{10}$ to $1 \times 10^{12}$ cells, spores or other propagules per gram.

In one embodiment, the microbial slurry is homogenized and dried to produce a dry microbe-based product. Drying can be performed using standard methods in the art, including, for example, spray drying, lyophilization, or freeze drying. In one embodiment, the dried product has approximately 3% to 6% moisture retention.

In one embodiment, the microbial slurry can be utilized directly, without drying or processing. In another embodiment, the microbial slurry can be mixed with water to form a liquid microbe-based product.

In some embodiments, the various formulations of microbe-based product produced according to the subject methods can be stored prior to their use.

In one embodiment, the systems and methods of the subject invention can be used to produce a microbial metabolite, wherein the microbial slurry is mixed with water or another solvent, and this slurry-solvent mixture is then filtered to separate solid portions of the mixture from liquid portions. The extracted liquid, which comprises the microbial metabolite, can then be purified further, if desired, using, for example, centrifugation, rotary evaporation, microfiltration, ultrafiltration and/or chromatography.

The metabolite and/or growth by-product can be, for example, a biosurfactant, enzyme, biopolymer, acid, solvent, amino acid, nucleic acid, peptide, protein, lipid, carbohydrate and/or other metabolite.

Specifically, in one embodiment, the method can be used to produce a biosurfactant. Even more specifically, in one embodiment, the method can be used to produce a glycolipid biosurfactant or a lipopeptide biosurfactant.

Advantageously, the method does not require complicated equipment or high energy consumption. The microorganisms of interest can be cultivated at small or large scale on site and utilized, even being mixed with their media. Similarly, the microbial metabolites can also be produced at large quantities at the site of need.

Advantageously, the microbe-based products can be produced in remote locations. The microbe growth facilities may operate off the grid by utilizing, for example, solar, wind and/or hydroelectric power.

Thermostable Enclosure System

In one embodiment, the fermentation reactor utilized in the subject methods can comprise a large, moisture-sealed, thermostable enclosed space, having four vertical walls, a floor and a ceiling. The walls can optionally comprise one or more windows and/or doors. This thermostable enclosure can replicate the environment that would exist in, for example, a proofing oven fermentation reactor, yet on a much larger scale.

In one embodiment, the thermostable enclosure is fixed onto a portable platform, such as a trailer with wheels.

In one embodiment, the interior of the thermostable enclosure comprises a plurality of horizontal surfaces, upon which the containers with inoculated matrix substrate can be placed.

In one embodiment, the surfaces are in the form of shelves. The shelves can be fixed onto the walls of the enclosure. Shelving units can also be suspended from the ceiling and/or fixed to the floor.

In one embodiment, the thermostable enclosure comprises a plurality of metal sheet pan racks. The sheet pan racks preferably comprise horizontal surfaces in the form of a plurality of slides for holding trays with inoculated matrix substrate. In one embodiment, the racks are portable, for example, fitted with wheels.

In one embodiment, the pan rack can hold from 10 to 50 trays. Preferably, the slides are spaced at least 3 inches apart from one another to allow for optimal air circulation between each tray when growing aerobic microbes.

In one embodiment, the ceiling of the enclosure can optionally be accommodated to allow for air flow, for example, with ceiling vents and/or air filters. Furthermore, the ceiling and walls can be fitted with UV lights to aid in sterilization of air and other surfaces within the system. Advantageously, the use of metal trays and metal pan racks enhances reflection of the UV light for increased UV sterilization.

In one embodiment, the thermostable enclosure can be equipped with standard temperature controls.

The dimensions of the thermostable enclosure can be customized based on various factors, such as, for example, the location of the enclosure and the number of containers to be placed therein. In one embodiment, the height of the ceiling is at least 8 feet, and the area of the floor is at least 80 square feet.

In one embodiment, the method of cultivating a microorganism and/or producing a microbial growth by-product comprises: a) placing a solid substrate, optionally mixed with nutrients to enhance microbial growth, into a container to form a matrix; b) applying an inoculant of a microorganism to the matrix; c) placing the container with inoculated matrix onto a horizontal surface, wherein the surface is inside a thermostable enclosure; and d) incubating the container with the inoculated matrix at a temperature between 25-40° C. for an amount of time to allow the microorganism to grow through the matrix.

In certain embodiments, the container is a sheet pan or tray, and the horizontal surface is a slide in a sheet pan rack. The tray can be places on the slides of the pan rack, along with a plurality of other inoculated trays. In one embodiment, a plurality of sheet pan racks filled with trays is used inside the thermostable enclosure.

Microbial Strains Grown in Accordance with the Subject Invention

The microorganisms produced according to the subject invention can be, for example, bacteria, yeasts and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In one embodiment, the microorganism is a yeast or fungus. Yeast and fungus species suitable for use according to the current invention, include *Acaulospora, Aspergillus, Aureobasidium* (e.g., *A. pullulans*), *Blakeslea, Candida* (e.g., *C. albicans, C. apicola, C. batistae, C. bombicola, C. floricola, C. kuoi, C. riodocensis, C. stellate*), *Debaryomyces* (e.g., *D. hansenii*), *Entomophthora, Glomus* (e.g., *G. mosseae*), *Hanseniaspora* (e.g., *H. uvarum*), *Hansenula, Issatchenkia, Kluyveromyces, Lentinula edodes, Mortierella, Mucor* (e.g., *M. piriformis*), *Penicillium, Phythium, Phycomyces, Pichia* (e.g., *P. anomala, P. guielliermondii, P. occidentalis, P. kudriavzevii*), *Pseudozyma* (e.g., *P. aphidis*), *Rhizopus, Rhodotorula* (e.g., *R. bogoriensis*); *Saccharomyces* (*S. cerevisiae, S. boulardii sequela, S. torula*), *Starmerella* (e.g., *S. bombicola*), *Torulopsis, Thraustochytrium, Trichoderma* (e.g., *T. reesei, T. harzianum, T. virens*), *Ustilago* (e.g., *U. maydis*), *Wickerhamiella* (e.g., *W. domericqiae*), *Wickerhamomyces* (e.g., *W. anomalus*), *Williopsis, Zygosaccharomyces*.

In one embodiment, the microorganism is a yeast known as a "killer yeast." As used herein, "killer yeast" means a strain of yeast characterized by its secretion of toxic proteins or glycoproteins, to which the strain itself is immune. Killer yeasts can include, but are not limited to species of, for example, *Candida* (e.g., *C. nodaensis*), *Cryptococcus, Debaryomyces* (e.g., *D. hansenii*), *Hanseniaspora*, (e.g., *H. uvarum*), *Hansenula, Kluyveromyces* (e.g., *K. phaffii*), *Pichia* (e.g., *P. anomala, P. guielliermondii, P. occidentalis, P. kudriavzevii*), *Saccharomyces* (e.g., *S. cerevisiae*), *Torulopsis, Ustilago* (e.g., *U. maydis*), *Wickerhamomyces* (e.g., *W. anomalus*), *Williopsis* (e.g., *W. mrakii*), *Zygosaccharomyces* (e.g., *Z. bailii*), and others.

In one embodiment, the microorganisms are bacteria, including Gram-positive and Gram-negative bacteria, as well as some archaea. The bacteria may be, spore-forming, or not. The bacteria may be motile or sessile. The bacteria may be anaerobic, aerobic, microaerophilic, facultative anaerobes and/or obligate aerobes. Bacteria species suitable for use according to the present invention include, for example, *Acinetobacter* (e.g., *A. calcoaceticus, A. venetianus*); *Agrobacterium* (e.g., *A. radiobacter*), *Azotobacter* (*A. vinelandii, A. chroococcum*), *Azospirillum* (e.g., *A. brasiliensis*), *Bacillus* (e.g., *B. amyloliquefaciens, B. firmus, B. laterosporus, B. licheniformis, B. megaterium, B. mucilaginosus, B. subtilis, B. coagulans* GBI-30 (BC30)), *Chlorobiaceae* spp., *Dyadobacter fermenters, Frankia* spp., *Frateuria* (e.g., *F. aurantia*), *Klebsiella* spp., *Microbacterium* (e.g., *M. laevaniformans*), *Pantoea* (e.g., *P. agglomerans*), *Pseudomonas* (e.g., *P. aeruginosa, P. chlororaphis, P. chlororaphis* subsp. *aureofaciens* (Kluyver), *P. putida*), *Rhizobium* spp., *Rhodospirillum* (e.g., *R. rubrum*), *Sphingomonas* (e.g., *S. paucimobilis*), and/or *Xanthomonas* spp.

The microbes and their growth products produced according to the subject invention can be used to produce a vast array of useful products, including, for example, biopesticides, biosurfactants, ethanol, nutritional compounds, therapeutic compounds (e.g. insulin, vaccines), and biopolymers.

In a specific embodiment, the microorganism is a killer yeast, such as *Wickerhamomyces anomalus* (*Pichia anomala*). *W. anomalus* is an effective producer of exo-β-1,3-glucanase, which allows for its use in controlling and/or inhibiting the growth of a wide spectrum of pathogenic fungi. Additionally, *W. anomalus* can produce various solvents, enzymes, killer toxins, as well as biosurfactants that are capable of reducing surface/interfacial tension of water, as well as exhibiting antimicrobial and antifungal properties.

The microorganism can also be another member of the *Wickerhamomyces* and/or *Pichia* clades (e.g., *Pichia guilliermondii* (*Meyerozyma guilliermondii*), *Pichia kudriavzevii* (*Wickerhamomyces kudriavzevii*), *Pichia occidentalis*).

*Pichia kudriavzevii* produces metabolites with antibacterial activity against several human and animal pathogens, such as *Escherichia coli, Enterococcus faecalis, Klebsiella* sp., *Staphylococcus aureus* and *Pseudomonas alcaligenes*. Furthermore, the toxins produced by *P. kudriavzevii* are capable of controlling many other Gram-positive and Gram-negative bacteria that can cause plant bacterial diseases.

Strains of *Pichia guilliermondii* produce hydrolytic enzymes, including β-1,3-glucanases and chitinases. These enzymes are known to have nematicidal (e.g., against *Meloidogyne incognita*) and antifungal (e.g. against *B. cinereal*) properties.

In addition to various by-products, *Pichia* yeasts are capable of producing phytase, a phosphatase enzyme that catalyzes the hydrolysis of phytic acid (phytate, or myo-inositol hexakisphosphate). Phytic acid is an indigestible, organic form of phosphorus that releases a usable form of inorganic phosphorus upon hydrolysis.

Additionally, *Pichia* yeasts are producers of a number of proteins (containing up to 50% of dry cell biomass), lipids and carbon sources, as well as a full spectrum of minerals and vitamins (B1; B2; B3 (PP); B5; B7 (H); B6; E).

In certain embodiments, the microorganism can be another yeast, such as *Starmerella bombicola* (capable of producing sophorolipids), *Pseudozyma aphidis* (capable of producing mannosylerythritol lipids) or *Saccharomyces boulardii*.

In one embodiment, the microorganism can be a fungus, such as a *Trichoderma* spp. fungus (e.g., *T. harzianum, T. viride, T. hamatum*, and/or *T. reesei*), or a mushroom-producing fungus (e.g., *Lentinula edodes* (shiitake)).

Certain species of *Trichoderma* fungi possess antagonistic properties towards various pests. A number of these fungi are useful when added to soil, where they can multiply and grow in close association with plants' roots. The *Trichoderma* can establish strong and long-lasting colonization of root surfaces, penetrating into the epidermis and shallow subsurface cells, where they are capable of protecting the roots from invasion by other plant pathogenic fungi and other microbial and animal pests, in addition to helping to stimulate plant growth.

Additionally, plants are protected from numerous classes of plant pathogen by responses that are similar to systemic acquired resistance and rhizobacteria-induced systemic resistance. *Trichoderma* spp. can effectively reduce diseases caused by some soil-borne plant pathogens. For example, the species *T. harzianum, T. hamatum*, and *T. viride* have fungicidal activity against *Sclerotium* spp, *Rhizoctonia, Solani, Pythium* spp, *Fusarium* spp, *Cercospora* spp, *Ralstonia* spp, *Fragaria* spp, *Rhizopus* spp, *Botrytis* spp, *Colletotrichum* spp, *Magnaporthe* spp. and many others. Moreover, some strains of *Trichoderma* are able to effectively suppress the growth of some viral and bacterial plant and soil pathogens, as well as produce some significant nematocidal effects.

In addition to protecting plants from pathogens and pests, root colonization by *Trichoderma* spp. frequently enhances root growth and development, crop productivity, resistance to abiotic stresses, and bioavailability of nutrients.

In one embodiment, the microorganism is a bacteria, such as *Pseudomonas* spp. (e.g., *P. aeruginosa, P. chlororaphis*), which can produce rhamnolipids.

In one embodiment, the microorganism is a bacteria, such a *Bacillus* spp. bacterium (e.g., *B. subtilis, B. licheniformis, B. firmus, B. laterosporus, B. megaterium, B. amyloliquefaciens* and/or *Bacillus coagulans* GBI-30 (BC30)).

In one embodiment, the microorganism is a strain of *B. subtilis*, such as, for example, *B. subtilis* var. *locuses* B1 or B2, which are effective producers of, for example, surfactin and other lipopeptide biosurfactants, as well as biopolymers. This specification incorporates by reference International Publication No. WO 2017/044953 A1 to the extent it is consistent with the teachings disclosed herein.

In preferred embodiments, these B series strains are characterized by enhanced biosurfactant production compared to wild type *Bacillus subtilis* strains. In certain embodiments, the *Bacillus subtilis* strains have increased biopolymer, solvent and/or enzyme production.

Furthermore, the B series strains can survive under high salt and anaerobic conditions better than other well-known *Bacillus* strains. The strains are also capable of growing under anaerobic conditions. The *Bacillus subtilis* B series strains can also be used for producing enzymes that degrade or metabolize oil or other petroleum products.

In certain embodiments, the microbe is *Bacillus licheniformis*, which is an effective producer of biosurfactants, as well as biopolymers, including, for example, levan.

Other microbial strains including, for example, strains capable of accumulating significant amounts of useful metabolites, such as, for example, biosurfactants, enzymes and biopolymers, can be used in accordance with the subject invention.

Compositions Produced According to the Subject Invention

The subject invention provides compositions comprising one or more microorganisms and/or one or more growth by-products thereof. In one embodiment, the composition comprises the matrix substrate containing the microorganism and/or the microbial metabolites produced by the microorganism and/or any residual nutrients. In some embodiments, the microbes of the composition are vegetative cells, or in spore, hyphae, mycelia and/or conidia form.

The product of fermentation may be used directly without extraction or purification. If desired, extraction and purification can be achieved using standard extraction methods or techniques known to those skilled in the art.

In one embodiment, the growth by-product is a biosurfactant. In one embodiment, the growth by-product is selected from any other microbial metabolite, including, for example, an enzyme, a biopolymer, a solvent, an acid, or a killer toxin.

Biosurfactants are a structurally diverse group of surface-active substances produced by microorganisms. Biosurfactants are biodegradable and can be easily and cheaply produced using selected organisms on renewable substrates. Most biosurfactant-producing organisms produce biosurfactants in response to the presence of a hydrocarbon source (e.g. oils, sugar, glycerol, etc.) in the growing media. Other media components such as concentration of iron can also affect biosurfactant production significantly.

All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces.

Biosurfactants accumulate at interfaces, thus reducing interfacial tension and leading to the formation of aggregated micellular structures in solution. The ability of biosurfactants to form pores and destabilize biological membranes permits their use as antibacterial, antifungal, and hemolytic agents. Combined with the characteristics of low toxicity and biodegradability, biosurfactants are advantageous for use in a variety of applications such as, for example, the agriculture and oil and gas industries.

Biosurfactants include low molecular weight glycolipids (GLs), lipopeptides (LPs), flavolipids (FLs), phospholipids, and high molecular weight polymers such as lipoproteins, lipopolysaccharide-protein complexes, and polysaccharide-protein-fatty acid complexes. The hydrocarbon chain of a fatty acid acts as the common lipophilic moiety of a biosurfactant molecule, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

Combined with the characteristics of low toxicity and biodegradability, biosurfactants can be useful in a variety of settings including, for example, oil and gas production; bioremediation and mining; waste disposal and treatment; animal health (e.g., livestock production and aquaculture); plant health and productivity (e.g., agriculture, horticulture, crops, pest control, forestry, turf management, and pastures); and human health (e.g., probiotics, pharmaceuticals, preservatives and cosmetics).

Thus, there exists an enormous potential for the use of microbial biosurfactants in a broad range of industries. One limiting factor in commercialization of these microbe-based products, however, has been the cost per propagule density, where it is particularly expensive and often unfeasible to cultivate efficacious microbial products on a large scale. Thus, the subject invention provides solutions to this problem through improved, scalable microbial fermentation systems and methods.

In one embodiment, the biosurfactants of the subject compositions include glycolipids such as rhamnolipids (RLP), sophorolipids (SLP), trehalose lipids (TL) and/or mannosylerythritol lipids (MEL).

In one embodiment, the growth by-product is a lipopeptide biosurfactant, including, for example, iturins, surfactins, fengycins, lichenysins and/or any family member thereof. Examples of lipopeptides according to the subject invention include, but are not limited to, surfactin, lichenysin, fengycin, polymyxin, iturin A, daptomycin, bacillomycin, mycosubtilin, fengycin A and B, plipastatin and chromobactymycin. In a specific embodiment, the lipopeptide is surfactin or iturin A.

Most biosurfactant-producing organisms produce biosurfactants in response to the presence of a hydrocarbon source (e.g., oils, sugar, glycerol, etc.) in the growing media. Other media components such as concentration of iron can also affect biosurfactant production significantly. Microbial biosurfactants are produced by a variety of microorganisms, such as, for example, *Pseudomonas* spp. (*P. aeruginosa, P. putida, P. florescens, P. fragi, P. syringae*); *Flavobacterium* spp.; *Bacillus* spp. (*B. subtilis, B. pumillus, B. licheniformis, B. amyloliquefaciens, B. cereus*); *Wickerhamomyces* spp. (e.g, *W. anomalus*), *Candida* spp. (e.g, *C. albicans, C. rugosa, C. tropicalis, C. lipolytica, C. torulopsis*); *Rhodococcus* spp.; *Arthrobacter* spp.; *Campylobacter* spp.; *Corynbacterium* spp.; *Pichia* spp. (e.g., *P. anomala, P. guilliermondii, P. occidentalis*); *Starmerella* spp. (e.g., *S. bombicola*); and so on.

In one embodiment, the microbial growth by-product is an enzyme, such as, for example, a phytase, a chitinase, a glucosidase and/or a glucanase (e.g., exo-β-1,3-glucanase). In one embodiment, the growth by-product is a biopolymer, such as, for example, levan, emulsan, xanthan gum, alginate, hyaluronic acid, PGAs, PHAs, cellulose, and lignin.

In one embodiment, the microbial growth by-product is a protein, a lipid, a carbon source, an amino acid, a mineral or a vitamin.

In certain embodiments, the compositions according to the subject invention can have advantages over, for example, purified microbial metabolites alone, due to, for example, the use of the entire culture. These can include, for example, high concentrations of mannoprotein as a part of yeast cell wall's outer surface (mannoprotein is a highly effective bioemulsifier) and the presence of biopolymer beta-glucan (an emulsifier) in yeast cell walls. Additionally, the compositions can comprise a variety of microbial metabolites in the culture, include biosurfactants, which are capable of reducing both surface and interfacial tension, and others (e.g., enzymes, lactic acid, ethyl acetate, ethanol, biopolymers, etc.).

In certain other embodiments, the compositions comprise one or more microbial growth by-products, wherein the growth by-product has been extracted from the culture and, optionally, purified. For example, in one embodiment, the substrate and microorganisms can be blended to form a thick slurry, which can be mixed with water or another solvent (e.g., saline), and filtered or centrifuged to separate the liquid portion from the solid portion. The liquid portion, comprising microbial growth by-products, can then be used as-is or purified using known methods.

Methods of Use

The compositions of the subject invention can be used for a variety of purposes. In one embodiment, the subject compositions can be highly advantageous in the context of the oil and gas industry. When applied to an oil well, wellbore, subterranean formation, or to equipment used for recovery oil and/or gas, the subject composition can be used in methods for enhancement of crude oil recovery; reduction of oil viscosity; removal and dispersal of paraffin from rods, tubing, liners, and pumps; prevention of equipment corrosion; recovery of oil from oil sands and stripper wells; enhancement of fracking operations as fracturing fluids; reduction of $H_2S$ concentration in formations and crude oil; and cleaning of tanks, flowlines and pipelines.

In one embodiment, the composition can be used to improve one or more properties of oil. For example, methods are provided wherein the composition is applied to oil or to an oil-bearing formation in order to reduce the viscosity of the oil, convert the oil from sour to sweet oil, and/or to upgrade the oil from heavy crude into lighter fractions.

In one embodiment, the composition can be used to clean industrial equipment. For example, methods are provided wherein the composition is applied to oil production equipment such as an oil well rod, tubing and/or casing, to remove heavy hydrocarbons, paraffins, asphaltenes, scales and other contaminants from the equipment. The composition can also be applied to equipment used in other industries, for example, food processing and preparation, agriculture, paper milling, and others where fats, oils and greases build up and contaminate and/or foul the equipment.

In one embodiment, the composition can be used in agriculture. For example, methods are provided wherein the composition is applied to a plant and/or its environment to treat and/or prevent the spread of pests and/or diseases. The composition can also be useful for enhancing water dispersal and absorption in the soil, as well as enhance nutrient absorption from the soil through plant roots, facilitate plant health, increase yields, and manage soil aeration.

In one embodiment, the composition can be used to enhance animal health. For example, methods are provided wherein the composition can be applied to animal feed or water, or mixed with the feed or water, and used to prevent the spread of disease in livestock and aquaculture operations, reduce the need for antibiotic use in large quantities, as well as to provide supplemental proteins and other nutrients.

In one embodiment, the composition can be used to prevent spoilage of food, prolong the consumable life of food, and/or to prevent food-borne illnesses. For example, methods are provided wherein the composition can be applied to a food product, such as fresh produce, baked goods, meats, and post-harvest grains, to prevent undesirable microbial growth.

Other uses for the subject compositions include, but are not limited to, biofertilizers, biopesticides, bioleaching, bioremediation of soil and water, wastewater treatment, nutraceuticals and supplements, cosmetic products, control of unwanted microbial growth, and many others.

Preparation of Microbe-Based Products

One microbe-based product of the subject invention is simply the substrate containing the microorganism and/or the microbial metabolites produced by the microorganism and/or any residual nutrients. Upon harvesting of the solid substrate, microbe, and/or by-products, the product can be homogenized, and optionally, dissolved in water, e.g., in a storage tank. In some embodiments, prior to dissolving in water, the product can be dried using, for example, spray drying or lyophilization. The dried product can also be stored.

The product of fermentation may be used directly without extraction or purification. If desired, extraction and purification can be achieved using standard extraction methods or techniques known to those skilled in the art.

The microorganisms in the microbe-based product may be in an active or inactive form. In some embodiments, the microorganisms have sporulated or are in spore form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

In one embodiment, the microbe-based product can comprise at least $1 \times 10^8$ to $1 \times 10^{12}$ cells, spores or other propagules per gram. In preferred embodiments, the product comprises at least $1 \times 10^{10}$ cells, spores or other propagules per gram.

The dried product and/or liquid product containing the dissolved culture can be transferred to the site of application via, for example, tanker for immediate use. Additional nutrients and additives can be included as well.

In other embodiments, the composition (in the form of a dried product or in dissolved liquid form) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

Upon harvesting the microbe-based composition from the reactors, further components can be added as the harvested product is processed and/or placed into containers for storage and/or transport. The additives can be, for example, buffers, carriers, other microbe-based compositions produced at the same or different facility, viscosity modifiers, preservatives, nutrients for microbe growth, tracking agents, pesticides, and other ingredients specific for an intended use.

Advantageously, in accordance with the subject invention, the microbe-based product may comprise the substrate in which the microbes were grown. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., an oil well). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used, for example, within 300 miles, 200 miles, or even within 100 miles. Advantageously, this allows for the compositions to be tailored for use at a specified location. The formula and potency of microbe-based compositions can be customized for a specific application and in accordance with the local conditions at the time of application.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1

Fermentation of Fungal Spores Using Corn Flour Substrate

For growing *Trichoderma* spp., 250 g of nixtamilized corn flour is mixed with deionized water and sterilized in a stainless steel steam pan sealed with a lid and pan bands. The pan with corn flour media is aseptically inoculated with *Trichoderma* seed culture then sealed with the lid and pan bands.

The pans are then incubated in a proofing oven at 30° C. for 10 days. After 10 days, approximately $1 \times 10^9$ to $1 \times 10^{10}$ propagules/g of *Trichoderma* are harvested. The harvested culture is homogenized and dried to form a dried microbe-based product.

Example 2

Fermentation of Fungal Spores Using Pasta Substrate

For growing *Trichoderma* spp., 250 grams of dry corn flour pasta mixed with 1000 L of water is placed onto stainless steel steam pans. The steam pans, pasta and water are then autoclaved to produce a "cooked" pasta substrate, and then sealed with sterilized lids and pan bands. The pasta-water substrate is then aseptically inoculated with *Trichoderma* seed culture.

The pans are incubated in the proofing oven at 30° C. for 8 days. After 8 days, approximately $1 \times 10^9$ to $1 \times 10^{10}$ propagules/g of *Trichoderma* are harvested. The harvested culture is homogenized and dried to form a dried microbe-based product.

Example 3

Fermentation of Yeast Using Foodstuff Substrate

A yeast fermentation product can be obtained via cultivation of *Wickerhamomyces anomalus* according to the subject methods. The matrix substrate comprises chickpeas, beans, soybeans, rice or other similar foodstuff.

The substrate is mixed with nutrient medium seeded with, for example, $1 \times 10^{12}$ cells/ml of *W. anomalus*. After about 3-5 days of growth at about 25-35° C., preferably, 28° C., the yeast and any growth by-products thereof (e.g., enzymes, solvents, and/or biosurfactants) can either be washed out and utilized in liquid form, optionally with further purification, or the yeast and substrate can be homogenized and optionally dried. The cell concentration of the dried product can be $1 \times 10^8$ to $1 \times 10^{12}$ cells per gram.

Example 4

Fermentation of *Bacillus* Spores

For *Bacillus* spp. spore production, a wheat bran-based media is used. The media is sterilized in stainless steel steam pans, then sealed with a lid and pan bands. Following sterilization, the pans are inoculated with seed culture and incubated in a proofing oven for 48-72 hours. At the end of fermentation, $1 \times 10^{10}$ spores/g of *Bacillus* are harvested.

Example 5

Solid State Fermentation of *Bacillus Subtilis* and *Bacillus Licheniformis*

*Bacillus subtilis* and *Bacillus licheniformis* can be cultivated using solid state fermentation methods. The medium comprises only corn flour (partially hydrolyzed corn meal) or wheat bran. Optionally, added nutrients are included to enhance microbial growth, such as, for example, salts, molasses, starches, glucose, sucrose, etc.

Foil-covered trays are autoclaved prior to inoculation. The culture medium is spread on the trays in a layer about 1 to 2 inches thick. Grooves and/or holes are made in the substrate to increase the surface area of the medium. To increase the speed of growth, i.e., increase the motility of the bacteria and distribution throughout the culture medium, potato extract and/or banana peel extract are added to the culture.

Spores of the *Bacillus* strain of choice are then sprayed onto the surface of the substrate and the trays are placed into a proofing oven. Fermentation inside the proofing oven occurs at a temperature between 32-40° C.

Dissolving the harvested product in water can produce product with at least $5 \times 10^9$ to $5 \times 10^{10}$ spores/ml. Nutrients can also be added to the end product, including, e.g., potassium salts (0.1% or lower), molasses and/or glucose (1-5 g/L), and nitrates.

Example 6

Fermentation of *Bacillus Subtilis* for Iturin a Production

A nutrient medium comprising the following components is prepared for growing *Bacillus subtilis* for iturin A production:

Mixture of polished rice and water (1:1.25, rice to water)
Soybean meal and/or corn step solids (80 g/L)
Maltose (67 g/L)
Potato extract (1%).

The nutrient medium components are mixed and placed in a container fitted with an air filter for aeration, then inoculated with *B. subtilis*. The containers, rice, water, and optional nutrients can then be sterilized by, for example, autoclaving. The heated rice creates a porous, sticky substrate. After preparation and sterilization, the containers are inoculated with the microorganism.

Fermentation is carried out in an incubator at 37° C. for 4 to 14 days. The fermentation medium and microorganisms are blended into a thick slurry, mixed with water or another solvent, and pressed through a filter to produce a liquid supernatant comprising microbial growth by-products, e.g., iturin A. This liquid can be centrifuged, or purified by other known means to extract and purify the iturin A.

What is claimed:

1. A method of cultivating a microorganism and/or producing a microbial growth by-product, the method comprising:
   a) placing a solid substrate, mixed with nutrients for microbial growth, into a container to form a matrix;
   b) applying an inoculant of the microorganism to the matrix;
   c) placing the container with the inoculated matrix into an incubation space; and
   d) incubating the container at a temperature between 25-40° C. for an amount of time to allow the microorganism to grow throughout the matrix, wherein the solid substrate comprises a plurality of pieces, morsels, grains or particles of rice, beans, legumes, lentils, corn, grains, pasta, oats, oatmeal, wheat bran, wheat flour, corn flour, nixtamilized corn flour, corn meal, and/or partially hydrolyzed corn meal.

2. The method of claim 1, wherein the incubation space is a proofing oven used in commercial baking.

3. The method of claim 1, wherein the incubation space is a thermostable enclosure comprising:
   a ceiling, a floor and four vertical walls;
   a ceiling vent for air flow; and
   UV lights.

4. The method of claim 1, wherein the inoculant comprises cells, spores or propagules of the microorganism, and wherein applying the inoculant comprises spraying, pouring or pipetting the inoculant onto the matrix.

5. The method of claim 1, wherein the microorganism requires oxygenation, and wherein the incubation space comprises an aeration system to provide slow motion air supply.

6. The method of claim 5, wherein the incubation space utilizes a passive air exchange system comprising an inlet, with an air filter, through which ambient air travels into the incubation space, and an outlet, through which air exits the incubation space.

7. The method of claim 1, wherein after the microorganism grows, the microorganism, growth by-products and substrate are harvested and blended into a slurry.

8. The method of claim 7, wherein the slurry is homogenized and dried to produce a dry microbe-based product.

9. The method of claim 7, wherein the dried microbe-based product comprises from $1\times10^8$ to $1\times10^{12}$ cells, spores or propagules per gram.

10. The method of claim 7, wherein dried microbe-based product is mixed with water to produce a liquid microbe-based product with a concentration of $1\times10^6$ to $1\times10^7$ CFU/ml.

11. The method of claim 7, wherein the slurry is mixed with a solvent to form a slurry-solvent mixture, and the slurry-solvent mixture is pressed through a filter to extract a liquid product comprising a biosurfactant.

12. The method of claim 1, wherein the microorganism is a yeast, fungus or bacteria.

13. The method of claim 12, wherein the microorganism is a yeast selected from *Wickerhamomyces anomalus*, *Pichia kudriavzevii*, *Pichia guilliermondii*, *Pichia occidentalis*, *Starmerella bombicola*, *Pseudozyma aphidis*, and *Saccharomyces boulardii*, or the microorganism is a bacteria selected from *Azotobacter* spp., *Pseudomonas* spp., and *Bacillus* spp.

14. The method of claim 13, wherein the *Bacillus* spp. are selected from *Bacillus subtilis*, *B. licheniformis*, *B. firmus*, *B. laterosporus*, *B. megaterium*, *B. amyloliquefaciens* and *Bacillus coagulans* GBI-30 (BC30).

15. The method of claim 12, wherein the microorganism is a fungus selected from *Lentinula edodes*, *Trichoderma reesei*, *Trichoderma harzianum*, *Trichoderma viride*, and *Trichoderma hamatum*.

16. A composition, produced according to the method of claim 1, wherein the composition comprises a microorganism and/or a growth by-product thereof, a substrate on which the microorganism was grown, and nutrients for microbial growth.

17. The composition of claim 16, wherein the growth by-product is a biosurfactant selected from sophorolipids, rhamnolipids, trehalose lipids, iturin, surfactin, fengycin, lichenysin and mannosylerythritol lipids.

18. The composition of claim 16, wherein the growth by-product is selected from levan, emulsan, xanthan gum, alginate, hyaluronic acid, PGAs, PHAs, cellulose, and lignin.

19. The composition of claim 16, wherein the growth by-product is selected a phytase, a chitinase, a glucosidase and/or a glucanase (e.g., exo-β-1,3-glucanase).

* * * * *